(12) United States Patent
Bonelli et al.

(10) Patent No.: US 10,414,123 B2
(45) Date of Patent: Sep. 17, 2019

(54) THREE-DIMENSIONAL COMPOSITE TAPE, METHOD AND APPARATUS FOR ITS PRODUCTION

(71) Applicant: Fameccanica.Data S.p.A., Pescara (IT)

(72) Inventors: Guido Bonelli, Pescara (IT); Domenico Polidori, Pescara (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 216 days.

(21) Appl. No.: 15/256,221

(22) Filed: Sep. 2, 2016

(65) Prior Publication Data

US 2017/0066219 A1    Mar. 9, 2017

(30) Foreign Application Priority Data

Sep. 8, 2015 (IT) .......................... 102015000049671

(51) Int. Cl.
*B32B 37/00* (2006.01)
*B32B 7/05* (2019.01)
(Continued)

(52) U.S. Cl.
CPC .......... *B32B 7/05* (2019.01); *A61F 13/15699* (2013.01); *A61F 13/15707* (2013.01);
(Continued)

(58) Field of Classification Search
CPC .......... B32B 7/045; B32B 3/30; B32B 5/022; B32B 5/26; B32B 37/0084;
(Continued)

(56) References Cited

U.S. PATENT DOCUMENTS 4,720,415 A * 1/1988 Vander Wielen ......... B32B 5/04
428/152
5,609,702 A * 3/1997 Andersen .......... A61F 13/15731
156/73.1
(Continued)

FOREIGN PATENT DOCUMENTS

EP    1090615 A1    4/2001
EP    1103240 A1    5/2001
(Continued)

OTHER PUBLICATIONS

Italian Search Report and Written Opinion dated Mar. 15, 2016 for Application No. ITUB20153482.

*Primary Examiner* — James D Sells
(74) *Attorney, Agent, or Firm* — Patterson + Sheridan, LLP

(57) ABSTRACT

A composite tape comprising a first web and a second web welded together according to a welding pattern comprising a plurality of welding points arranged in arrays extending along a first direction and spaced apart in a second direction, perpendicular to said first direction, with adjacent arrays offset from each other in said first direction, and with said welding points in each array arranged in groups spaced apart in said first direction, wherein the first web has a plurality of hollow protrusions alternating with welding points, both in said first direction and in said second direction, and wherein the second web has a plurality of ribs extending along said first direction and separated from each other by said arrays of welding points.

7 Claims, 4 Drawing Sheets

(51) Int. Cl.

| | | |
|---|---|---|
| *B32B 5/02* | (2006.01) | |
| *B32B 5/26* | (2006.01) | |
| *B32B 3/30* | (2006.01) | |
| *A61F 13/511* | (2006.01) | |
| *A61F 13/15* | (2006.01) | |
| *B29C 65/08* | (2006.01) | |
| *B29C 65/00* | (2006.01) | |
| *B29C 65/02* | (2006.01) | |
| *B32B 37/06* | (2006.01) | |
| *B29L 31/48* | (2006.01) | |
| *B32B 37/20* | (2006.01) | |
| *B32B 38/06* | (2006.01) | |

(52) U.S. Cl.
CPC .. *A61F 13/15731* (2013.01); *A61F 13/15739* (2013.01); *A61F 13/5116* (2013.01); *A61F 13/51104* (2013.01); *B29C 65/02* (2013.01); *B29C 65/086* (2013.01); *B29C 66/1122* (2013.01); *B29C 66/21* (2013.01); *B29C 66/41* (2013.01); *B29C 66/45* (2013.01); *B29C 66/7294* (2013.01); *B29C 66/81433* (2013.01); *B29C 66/83411* (2013.01); *B29C 66/83415* (2013.01); *B29C 66/93411* (2013.01); *B32B 3/30* (2013.01); *B32B 5/022* (2013.01); *B32B 5/26* (2013.01); *B32B 37/0084* (2013.01); *A61F 2013/51178* (2013.01); *A61F 2013/51182* (2013.01); *B29L 2031/4878* (2013.01); *B32B 37/0053* (2013.01); *B32B 37/065* (2013.01); *B32B 37/20* (2013.01); *B32B 38/06* (2013.01); *B32B 2309/14* (2013.01); *B32B 2310/028* (2013.01); *B32B 2555/02* (2013.01)

(58) Field of Classification Search
CPC .......... A61F 13/15699; A61F 13/15707; A61F 13/15731; A61F 13/15739; A61F 13/51104; A61F 13/5116; B29C 65/02; B29C 65/086; B29C 66/1122; B29C 66/21; B29C 66/41; B29C 66/45
USPC ....................................................... 156/73.1
See application file for complete search history.

(56) References Cited

U.S. PATENT DOCUMENTS

| | | |
|---|---|---|
| 2010/0249740 A1 | 9/2010 | Miyamoto et al. |
| 2014/0000795 A1 | 1/2014 | Hamilton et al. |

FOREIGN PATENT DOCUMENTS

| | | |
|---|---|---|
| EP | 1419754 A1 | 5/2004 |
| EP | 2856994 A1 | 4/2015 |
| WO | 2013068868 A1 | 5/2013 |
| WO | 2015041929 A1 | 3/2015 |

\* cited by examiner

THREE-DIMENSIONAL COMPOSITE TAPE, METHOD AND APPARATUS FOR ITS PRODUCTION

CROSS-REFERENCE TO RELATED APPLICATIONS

This application claims benefit of Italian patent application number 102015000049671, filed Sep. 8, 2015, which is herein incorporated by reference.

BACKGROUND OF THE INVENTION

Field of the Invention

The present invention relates to a three-dimensional composite tape usable in particular to form the topsheet of absorbent sanitary articles. The invention also relates to a method and an apparatus for producing a three-dimensional composite tape.

Description of Prior Art

The topsheet of absorbent sanitary articles is usually formed of a sheet of permeable material, generally fibrous, typically of non-woven fabric, configured to transfer body fluids toward an absorbent core encased between the topsheet and a backsheet impermeable to body fluids.

In more traditional solutions, the topsheet of an absorbent sanitary article is formed of a smooth sheet. There are also known composite sheets with a three-dimensional structure intended to form the topsheet of absorbent sanitary articles. For example, EP-A-1419754 describes a composite sheet comprising an upper layer and a lower layer, both made of an essentially inextensible sheet, which are partially welded together at a large number of welds. The upper layer forms a large number of hollow protrusions in the areas different from the welds, formed by reliefs of the upper layer that enclose respective empty volumes. The lower layer has a flat shape. The formation of the hollow projections of the upper layer is obtained by subjecting the upper layer to an embossing step prior to the mutual welding between the upper layer and the lower layer.

SUMMARY OF THE INVENTION

The present invention aims to provide a three-dimensional composite tape for the topsheet of absorbent sanitary articles, having a greater versatility of use with respect to known types of three-dimensional composite tapes. The invention also aims to provide a method and an apparatus for producing an improved three-dimensional composite sheet.

According to the present invention, these aims are achieved by a three-dimensional composite tape, by a method and by an apparatus having the characteristics forming the subject of the claims.

The claims form an integral part of the disclosure given in relation to the invention.

BRIEF DESCRIPTION OF THE DRAWINGS

The present invention will now be described in detail with reference to the attached drawings, given purely by way of non-limiting example, in which.

DETAILED DESCRIPTION

Figure 1:
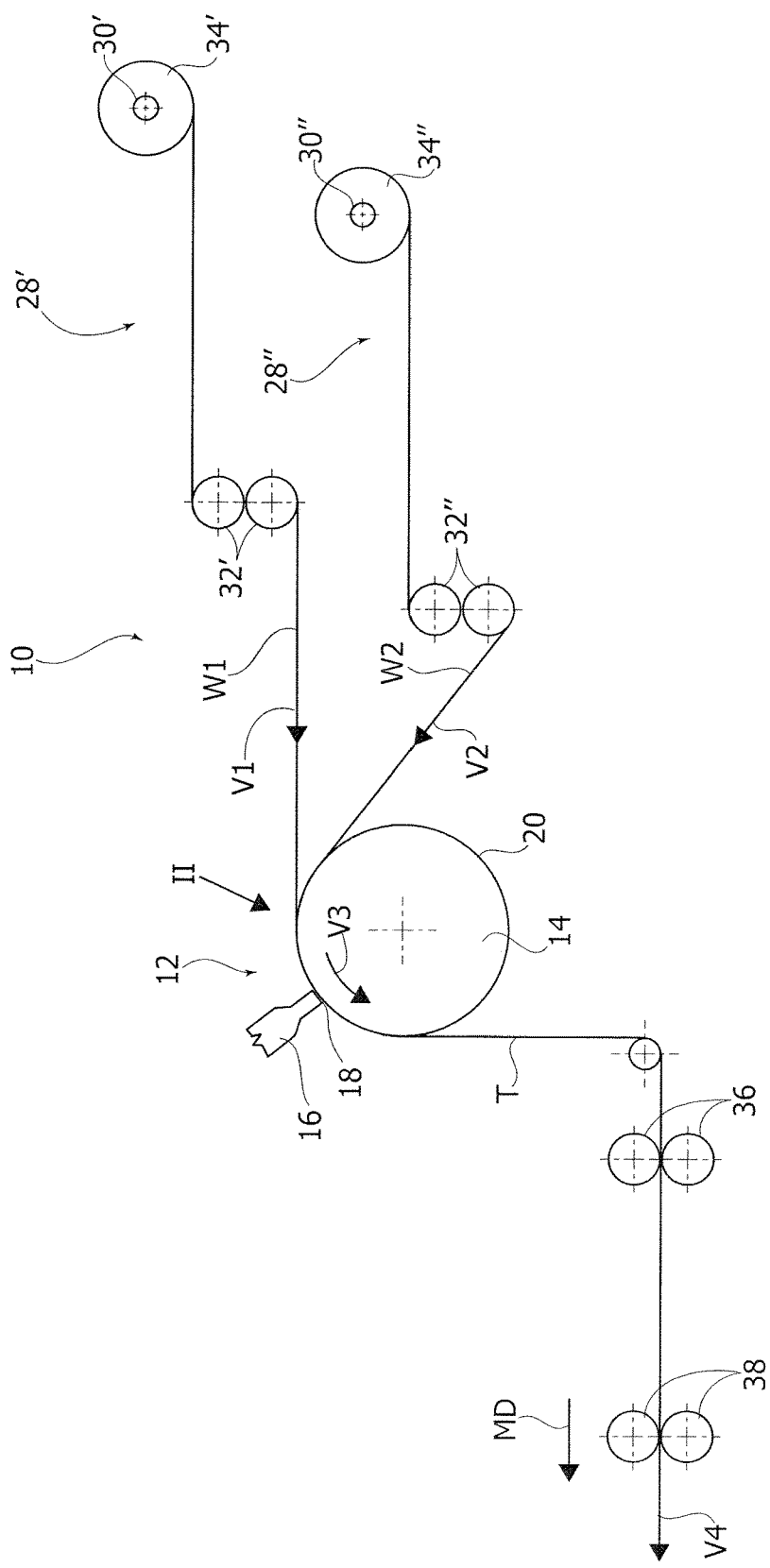
FIG. 1 is a schematic view of a first embodiment of an apparatus for producing a three-dimensional composite tape according to the present invention.

With reference to FIG. 1, numeral 10 indicates an apparatus for producing a three-dimensional composite tape suitable for forming the topsheet of absorbent sanitary products. The apparatus 10 comprises a welding unit 12 including an anvil roller 14 and a welding element 16 cooperating with the peripheral surface of the anvil roller 14. The welding element 16 can be, for example, a sonotrode of an ultrasonic welding unit. The welding element 16 and the anvil roller 14 define a welding gap 18. The anvil roller 14 rotates around its own axis at a controlled speed.

Figure 2:
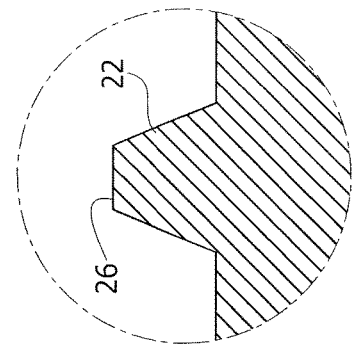
FIG. 2 is a perspective view of a welding roller indicated by the arrow II in FIG. 1.
Figure 3:
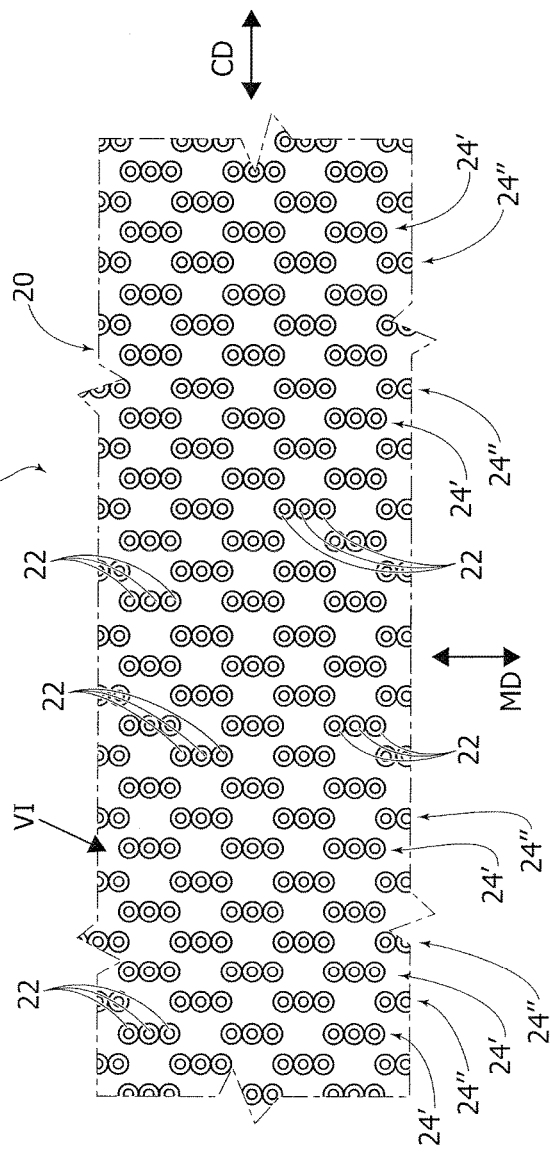
FIG. 3 is a plane development of the perimetral surface of the welding roller of FIG. 2.

With reference to FIGS. 2 and 3, the anvil roller 14 has a peripheral surface 20 provided with welding projections 22. As illustrated in greater detail in FIG. 3, the welding projections 22 are arranged in first and second arrays 24', 24" extending along a first direction and spaced apart from each other, preferably by a constant pitch, in a second direction perpendicular to the first direction and with adjacent arrays 24', 24" offset from each other in the first direction MD. In the illustrated example, the first direction is the machine direction MD or longitudinal direction, and the second direction is the cross machine direction CD.

In an alternative embodiment, the arrangement of the arrays 24', 24" could be rotated by 90° with respect to that illustrated. In this alternative embodiment, the arrays 24', 24" extend in a cross machine direction CD and are spaced apart in the machine direction MD.

Each array 24', 24" comprises a plurality of groups of welding projections 22. Each group comprises a plurality of welding projections 22 close together and aligned with each other in the first direction MD. The individual groups of welding projections of each array 24', 24" are spaced apart in the first direction MD, preferably by a constant pitch.

Figure 4:
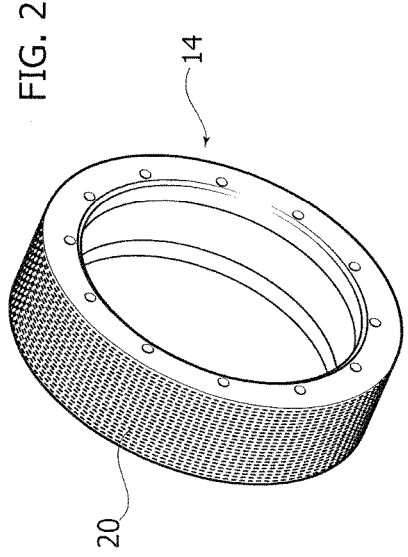
FIG. 4 is a detail in cross-section of the part indicated by the arrow VI in FIG. 3.

In the illustrated example, each welding projection 22 has the shape of a frusto-conical pin converging upwards, as illustrated in FIG. 4. Each welding projection 22 has a front surface 26 that cooperates with the welding element 16 to carry out a respective welding point. The front surfaces 26 of the welding projections 22 define a welding pattern with a shape corresponding to the plane development of the peripheral surface 20.

With reference to FIG. 1, the apparatus 10 comprises two feed units 28', 28", each of which is configured to feed a respective web W1, W2 to the welding unit 12. The material constituting the webs W1, W2 is a permeable material, generally fibrous, of the type commonly used for producing the topsheet of absorbent sanitary products. Each feed unit 28', 28" comprises an unwinding reel 30', 30" and a pair of feed rollers 32', 32" that feed the respective webs W1, W2 at respective speeds V1, V2, controlled by a control unit.

Respective spools 34', 34" formed by respective wound webs W1, W2 are positioned on the unwinding reels 30', 30".

The overlapping webs W1, W2 are fed to the welding gap 18 of the welding unit 12 with respective speeds V1, V2 different from each other. The peripheral surface 20 of the anvil roller 14 has a peripheral speed V3. The welding unit 12 welds together the initially smooth webs W1, W2 with a welding pattern corresponding to the distribution of the welding projections 22 of the anvil roller 14.

At the outlet of the welding unit 12, a composite tape T is formed that is fed in a machine direction MD to a machine for producing absorbent sanitary articles. The composite tape T is fed in the machine direction MD at a speed V4 by means of a first and a second pair of feed rollers 36, 38.

The webs W1, W2 can be made of non-woven fabric with a weight of 20-30 g/m$^2$. For example, the webs W1, W2 could be made of the material produced by JINLANG with the code AS120, with a weight of 20 g/m$^2$, or of the material produced by TEXUS with the code ABT30TTE, with a weight of 30 g/m$^2$. The two webs W1, W2 can be made of the same material or of different materials.

Suitable materials for producing a three-dimensional composite tape T according to the present invention should have a permanent residual deformation between 5 and 10% after an elongation of 16%, measured according to the WSP 110.4 standard (Standard Test Method for Breaking Force and Elongation of Non-Woven Fabric). This test envisages the use of sample with a length of 200 mm in the longitudinal direction (MD) and a width of 50 mm in the cross direction (CD). The ends of the sample are clamped between two clamps spaced apart by 100 mm, which are moved apart at a speed of 100 mm/min. After an elongation of the material by 16%, the permanent residual deformation of the material is measured in the absence of load.

With this test, the JINLANG AS120 material has a permanent residual deformation of around 6%. The TEXUS ABT30 TTE material has a permanent residual deformation of around 9%.

With reference to FIG. 1, the speeds V1, V2 of the webs W1, W2 are controlled in relation to the peripheral speed V3 of the anvil roller 14. In particular, the ratio V1/V3 between the advancing speed of the first web W1 and the peripheral speed V3 of the anvil roller 14 is between 0.8 and 1.2, preferably between 0.9 and 1.05, and even more preferably between 0.98 and 1. The V2/V3 ratio between the advancing speed of the second web W2 and the peripheral speed V3 of the anvil roller 14 is between 0.75 and 0.95, preferably between 0.80 and 0.90 and even more preferably between 0.84 and 0.86.

The ratio V4/V3 between the speed V4 with which the composite strip S is fed to the forming machine of absorbent sanitary products and the peripheral speed V3 of the anvil roller 14 is between 0.85 and 1, and preferably between 0.90 and 0.95. The web W2 with a lower speed (and therefore with higher tensioning) is preferably immediately in contact with the peripheral surface of the anvil roller 14 while the web W1 with a higher speed is arranged above the web W2. In this way, the web W2 with a higher tensioning is also subject to a greater retaining action by the peripheral surface 20 of the anvil roller 14 thanks to the anchoring action of the welding projections 22.

Figure 7:
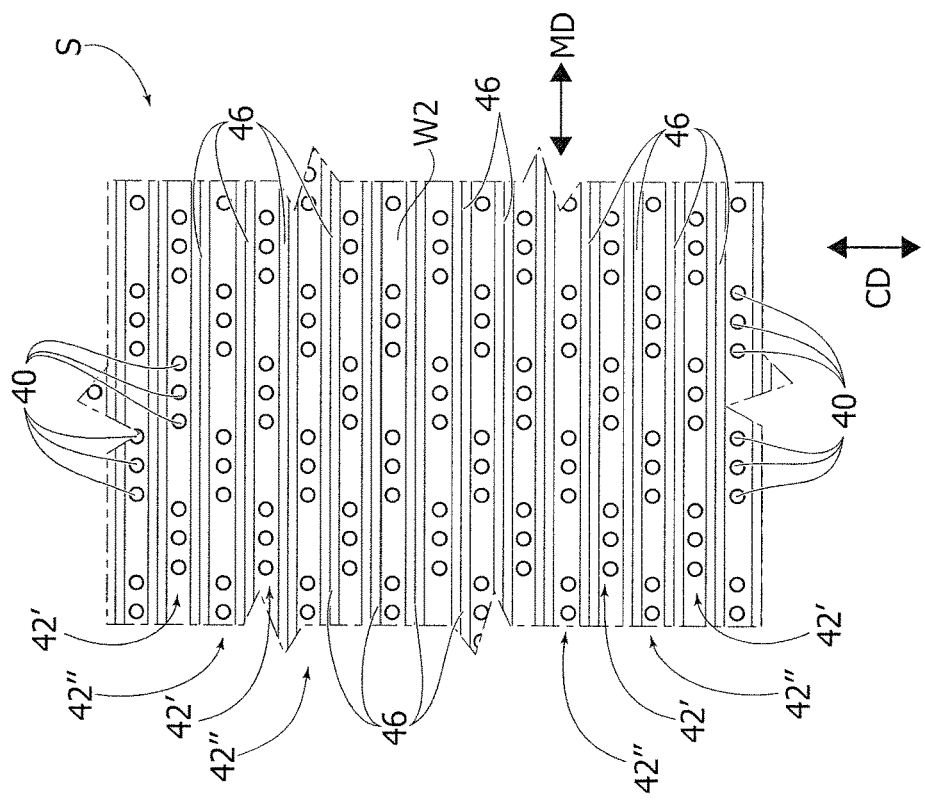
FIG. 7 is a schematic plan view of the second side of the three-dimensional composite tape according to the present invention.
Figure 6:
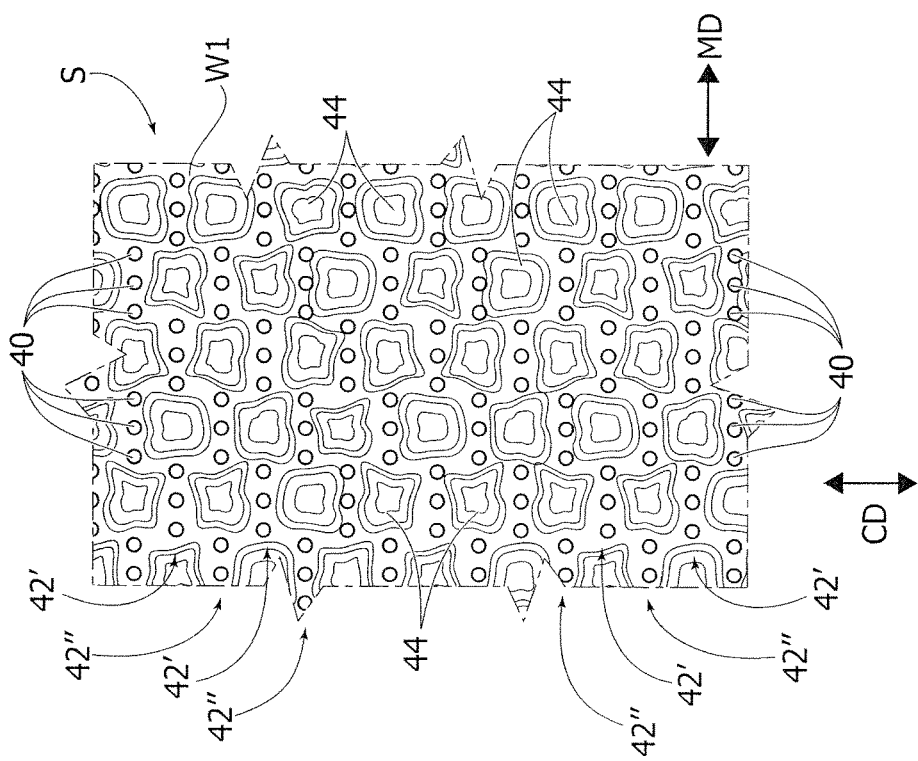
FIG. 6 is a schematic plan view of a first side of a three-dimensional composite tape according to the present invention.

FIGS. 6 and 7 schematically show the three-dimensional composite sheet T in plan view from the side of the web W1 and from the side of the web W2. The two webs W1 and W2 are welded together using a welding pattern that comprises a plurality of welding points 40 arranged in arrays 42', 42" extending along a first direction (MD) and spaced apart in a second direction (CD) perpendicular to the first direction. In the illustrated example, the first direction is the machine direction MD or longitudinal direction and the second direction is the cross machine direction CD.

In an alternative embodiment, the arrangement of the arrays 42', 42" could be rotated by 90° with respect to that illustrated. In this alternative embodiment, the arrays 42', 42" extend in a cross machine direction CD and are spaced apart by a constant pitch in the machine direction MD.

The adjacent arrays 42', 42' are offset from each other in the first direction MD. In each array 42', 42", the welding points 40 are arranged in groups and each group is spaced apart from an adjacent group in the first direction MD, preferably by a constant pitch.

The three-dimensional composite tape T according to the present invention has different surface finishes on opposite sides. On the first web W1, hollow protrusions 44 are provided, formed by reliefs of the first web W1 that enclose respective empty volumes. The hollow protrusions 44 are spaced from each other both in the first direction MD and in the second direction CD. Longitudinal ribs 46 are formed on the second web W2, which are parallel to each other, extend in the first direction MD, and are spaced apart in the second direction CD. This different surface finishing of the opposing faces of the composite sheet allows the composite tape T to be used with the web W1 facing towards the user or, vice versa, with the web W2 facing towards the user, depending on the tactile effect required. For example, for smaller absorbent sanitary products (intended to be used by smaller children) the topsheet can be placed with the web W2 facing towards the user to take advantage of the channels between the ribs 46 to keep the skin of the child drier. For larger absorbent sanitary products (intended to be used by larger children) the topsheet can be placed with the web W1 facing towards the user's skin to exploit the greater absorbent capacity of the hollow formations 44.

Figure 5:
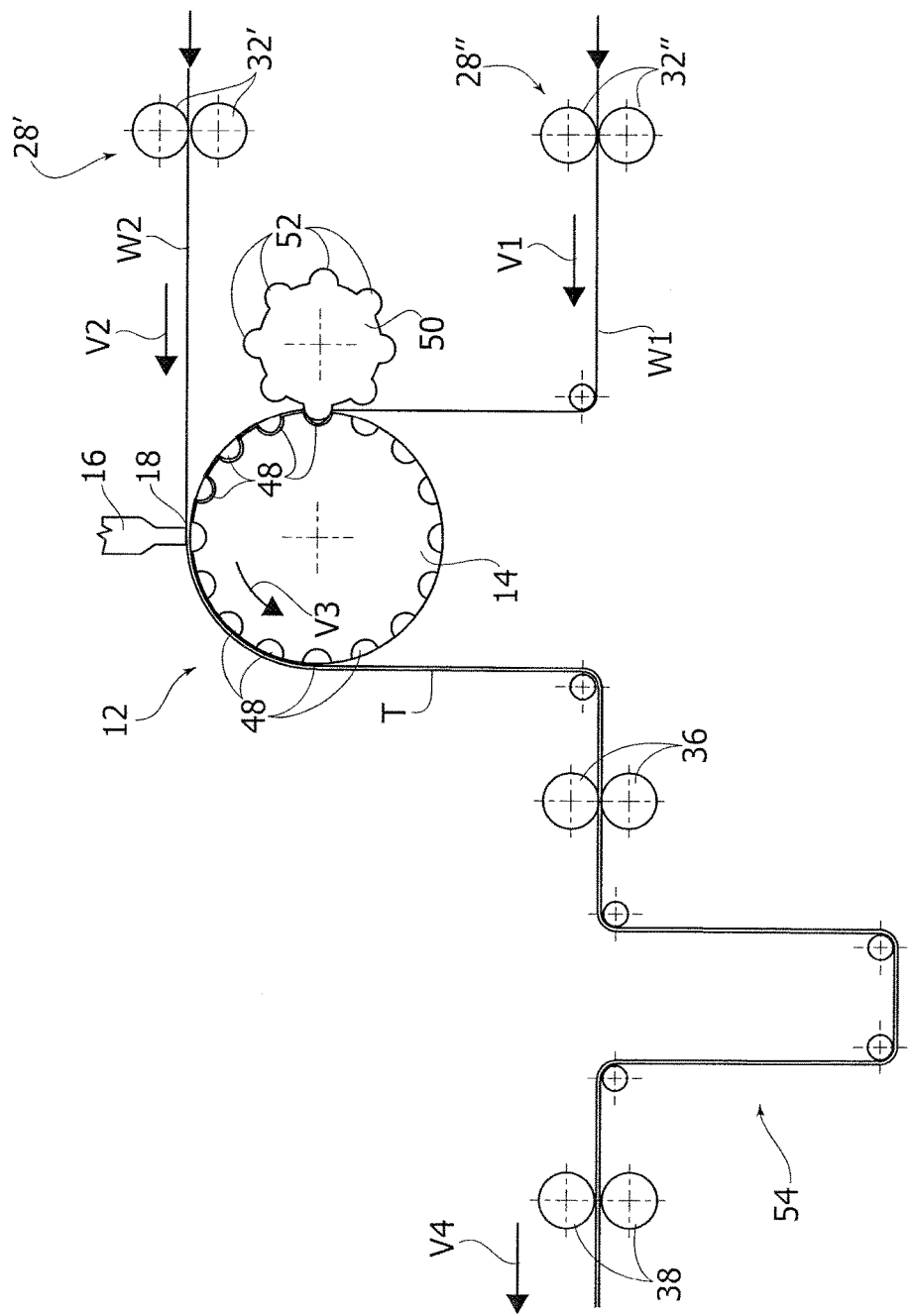
FIG. 5 is a schematic view of a second embodiment of an apparatus for producing a three-dimensional composite tape according to the present invention.

FIG. 5 illustrates a second embodiment of an apparatus according to the present invention. The elements corresponding to those previously described are indicated by the same reference numerals.

In this second embodiment, the web W1 is subjected to an embossing before welding with the web W2. In this second embodiment, the anvil roller 14 has a plurality of recesses 48 on its perimetral surface. The recesses are an alternative to the arrays of welding projections 22. The recesses 48 are distributed on the perimetral surface of the anvil roller 14, spaced apart both in the circumferential direction and in the cross direction. The anvil roller 14 cooperates with an embossing roller 50 provided on its outer surface with a plurality of projections 52, complementary to the recesses 48 of the anvil roller 14. In this second embodiment, the web W1 with a higher speed is subjected to the preliminary embossing operation, and is directly in contact with the perimetral surface of the anvil roller 14 while the web W2 with a lower speed is arranged above the first web W1. The welding between the first and the second webs W1, W2 is carried out with a welding pattern corresponding to that previously described, whereby the three-dimensional composite tape T obtained has a structure similar to that of the three-dimensional composite sheet T shown in FIGS. 6 and 7.

In this second embodiment the ratio V1/V3 can be between 1 and 1.3 and preferably between 1.15 and 1.25, while the V2/V3 ratio can be between 0.8 and 0.9. The advancing speed V4 in the machine is the speed that results from the recovery of the tensioning of the composite tape T.

The speed V4 is always less than the peripheral speed of the anvil roller 14 and depends on the depth of the recesses 48 in which the web W1 is formed. In this embodiment, a buffer 54 can be provided, arranged between the first pair of feed rollers 36 and the second pair of feed rollers 38.

Of course, without altering the principle of the invention, the details of construction and embodiments may be varied widely with respect to those described and illustrated without thereby departing from the scope of the invention as defined by the claims that follow.

The invention claimed is:

1. A method for producing a composite tape, comprising the steps of:
arranging a welding unit including an anvil roller and a welding element defining a welding gap therebetween,
advancing a first and a second web in direct contact with each other through the welding gap, and
welding directly together only the first and the second webs with a welding pattern comprising a plurality of welding points arranged in arrays extending along a first direction and spaced apart in a second direction perpendicular to the first direction, with adjacent arrays offset from each other in the first direction, and with the welding points in each array arranged in groups spaced apart in the first direction at a first distance greater than a second distance between individual welding points within each group, wherein:
the advancing speed of the first web towards the welding unit and the advancing speed of the second web towards the welding unit are different from each other and wherein the advancing speed of at least one of the webs is less than the peripheral speed of the anvil roller.

2. A method according to claim 1, wherein the first and the second webs are both smooth upstream of the welding gap.

3. A method according to claim 1, wherein the web advancing at a greater speed is subjected to an embossing step upstream of the welding gap.

4. A method according to claim 2, wherein the ratio between the advancing speed of the first web and the peripheral speed of the anvil roller is between 0.8 and 1.2, and wherein the ratio between the advancing speed of the second web and the peripheral speed of the anvil roller is between 0.75 and 0.95.

5. A method according to claim 3, wherein the ratio between the advancing speed of the first web and the peripheral speed of the anvil roller is between 1 and 1.3 and preferably between 1.15 and 1.25, and wherein the ratio between the advancing speed of the second web and the peripheral speed of the anvil roller is between 0.8 and 0.9.

6. A method according to claim 1, wherein the first direction is a machine direction.

7. A method according to claim 1, wherein the first direction is a cross direction to a machine direction.

* * * * *